US00RE33925E

United States Patent [19]

Bales et al.

[11] E Patent Number: Re. 33,925

[45] Reissued Date of Patent: May 12, 1992

[54] ELECTROSURGICAL CATHETER AND METHOD FOR VASCULAR APPLICATIONS

[75] Inventors: Thomas O. Bales, Coral Gables; Kevin W. Smith, Miami, both of Fla.

[73] Assignee: Cordis Corporation, Miami Lakes, Fla.

[21] Appl. No.: 281,063

[22] Filed: Dec. 8, 1988

Related U.S. Patent Documents

Reissue of:

[64] Patent No.: 4,682,596
Issued: Jul. 28, 1987
Appl. No.: 612,879
Filed: May 22, 1984

[51] Int. Cl.[5] ..... A61B 17/36

[52] U.S. Cl. ..... 606/48; 606/50

[58] Field of Search ..... 606/48-50; 128/4-8, 399-402, 783, 784, 786

[56] References Cited

U.S. PATENT DOCUMENTS

| | | | |
|---|---|---|---|
| Re. 27,569 | 2/1973 | Ackerman | 128/418 |
| 452,220 | 5/1891 | Gunning | 128/786 |
| 552,832 | 1/1896 | Fort . | |
| 623,022 | 4/1899 | Johnson . | |
| 1,677,642 | 7/1928 | Kirk . | |
| 3,301,258 | 1/1967 | Werner et al. | 128/303.1 |
| 3,348,548 | 10/1967 | Churdeck | 128/786 |
| 3,494,364 | 2/1970 | Peters | 128/399 |
| 3,532,095 | 10/1970 | Miller et al. | 128/303.13 |
| 3,595,239 | 7/1971 | Peterson | 128/303.14 |
| 3,698,394 | 10/1972 | Piper et al. | 128/303.1 |
| 3,798,967 | 3/1974 | Gieles et al. | 73/204 |
| 3,920,021 | 11/1975 | Hittebrandt | 606/50 |
| 4,030,508 | 6/1977 | Thalen | 128/786 |
| 4,038,519 | 7/1977 | Foucras | 219/301 |
| 4,043,342 | 8/1977 | Morrison | 128/303.14 |
| 4,060,086 | 11/1977 | Storz | 128/303.15 |
| 4,116,198 | 9/1978 | Roos | 606/48 |
| 4,132,227 | 1/1979 | Ibe | 128/4 |
| 4,142,529 | 3/1979 | Latenser et al. | 128/401 |
| 4,146,019 | 3/1979 | Bass et al. | 128/6 |
| 4,176,659 | 12/1979 | Rolfe | 128/635 |
| 4,207,874 | 6/1980 | Choy | 128/6 |
| 4,217,910 | 8/1980 | Khalil | 128/670 |
| 4,227,535 | 10/1980 | Conner | 128/401 |
| 4,240,441 | 12/1980 | Khalil | 128/692 |
| 4,347,842 | 9/1982 | Beale | 128/276 |
| 4,423,727 | 1/1984 | Widran et al. | 128/303.15 |
| 4,429,694 | 2/1984 | McGreevy | 128/303.14 |
| 4,438,766 | 3/1984 | Bowers | 128/303.14 |
| 4,449,528 | 5/1984 | Auth et al. | 128/303.1 |
| 4,517,975 | 5/1985 | Garito et al. | 128/303.13 |
| 4,524,770 | 6/1985 | Orandi | 128/303.1 |
| 4,532,924 | 8/1985 | Auth et al. | 606/50 |
| 4,534,366 | 8/1985 | Sowkeys | 128/786 |

FOREIGN PATENT DOCUMENTS

| | | | |
|---|---|---|---|
| 2315075 | 12/1974 | Fed. Rep. of Germany | 128/303.1 |
| 2535341 | 12/1976 | Fed. Rep. of Germany | 128/50 |
| 2060397 | 5/1981 | United Kingdom | 128/303.1 |
| 2071500 | 9/1981 | United Kingdom | 128/303.1 |

OTHER PUBLICATIONS

"Transarterial Elec. . . . of the Pancreas", Oct. 1975, Gold et al., Am. J. Roent.

*Primary Examiner*—Max Hindenburg
*Attorney, Agent, or Firm*—Henry W. Collins; Thomas R. Vigil

[57] ABSTRACT

The method for resolving atherosclerotic plaque buildup and/or eroding unwanted tissue in a blood vessel includes the steps of: inserting an electrode in and along the lumen of a blood vessel; manually manipulating said electrode through the blood vessel; positioning said electrode proximate to atherosclerotic plaque buildup site or unwanted tissue site in the blood vessel; supplying a predetermined high-frequency, high-voltage electrical current to said electrode; maintaining said predetermined current for a predetermined time period; and sensing from time to time, the amount of plaque or unwanted tissue at the site.

The electrosurgical plaque-resolving or tissue-eroding device is adapted to be inserted within and along the lumen of a blood vessel and manipulated therethrough to a desired position where the device is operated to resolve atherosclerotic plaque buildup or erode tissue in the blood vessel according to the method to re-establish desired blood flow through the blood vessel or to remove tissue therefrom. The device comprises an elongate flexible hollow tubular body having a distal end and a proximal end. A hollow tip member is mounted at the distal end of the flexible hollow tubular body and an electrode is associated with the hollow tip member for resolving plaque or eroding tissue. A power supply circuit for supplying a high-frequency, high-voltage electrical current to the electrode is coupled to the electrode. A mechanism for sensing, from time to time, the amount of plaque or tissue at the site in the blood vessel is also provided with the device.

47 Claims, 3 Drawing Sheets

FIG. 5
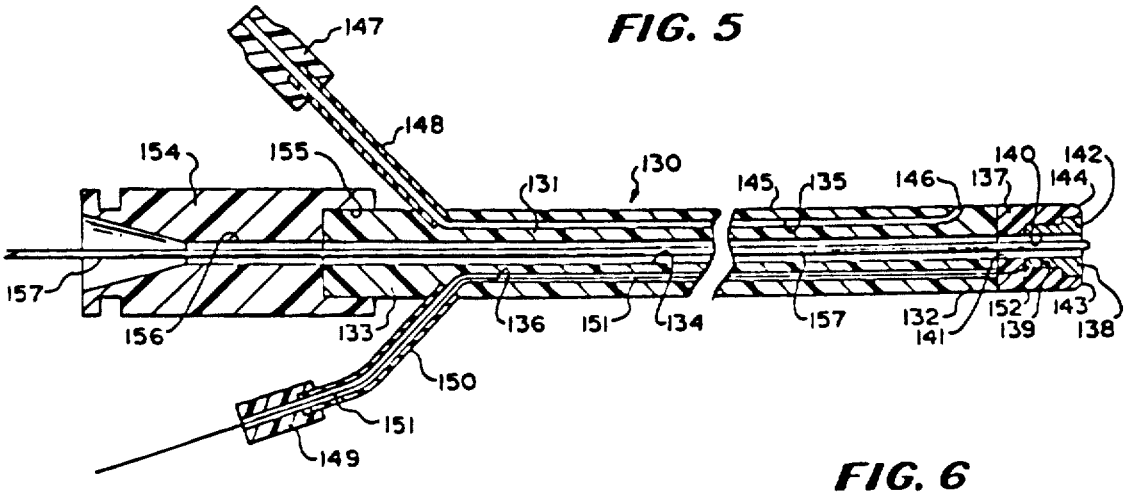
FIG. 6
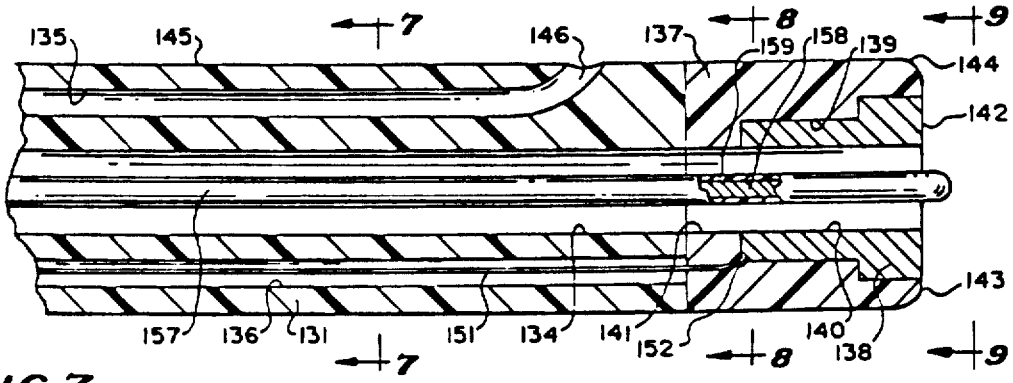
FIG. 7
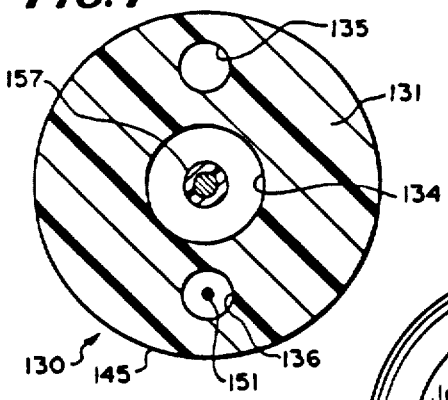
FIG. 8
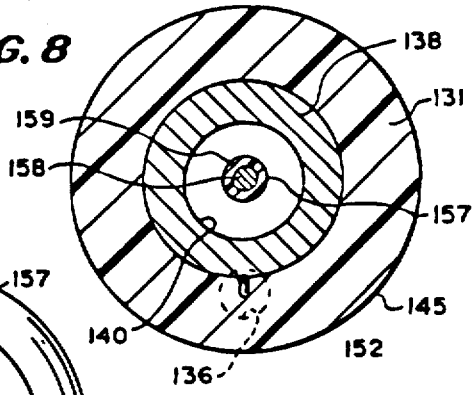
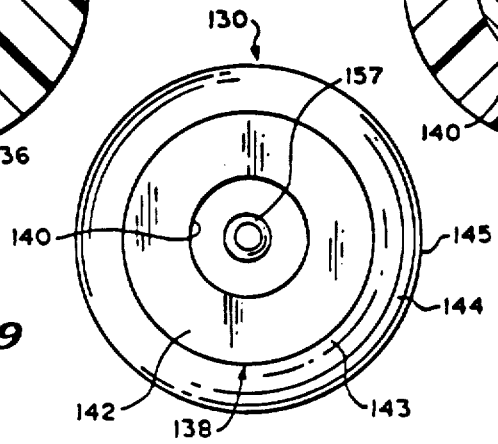
FIG. 9

ELECTROSURGICAL CATHETER ANED METHOD FOR VASCULAR APPLICATIONS

Matter enclosed in heavy brackets [ ] appears in the original patent but forms no part of this reissue specification; matter printed in italics indicates the additions made by reissue.

*This application is a reissue of 06/612,879 filed May 22, 1984, Pat. No. 4,682,596.*

BACKGROUND OF THE INVENTION

1. Field of the Invention

The present invention relates to a device and method for resolving or removing atherosclerotic plaque buildup or tissue in a blood vessel in order to restore necessary blood flow. The device includes a hollow catheter with a hollow tip member having an electrode for actively eroding, by means of high frequency high voltage electric current, atherosclerotic plaque areas or unwanted tissue within a blood vessel. The current generated at the electrode through the fatty material resolves the fatty material of the plaque and the residue of same may be removed through the hollow catheter.

2. Description of the Prior Art

Heretofore, various body insertable devices, such as catheters, having means for delivering impulses of electric current have been proposed for delivering electric current to internal organs, cavities or orifices of a body.

Such devices have generally been used with one electrode external of the body, and with means for delivery of irrigant fluid to or from the body.

Examples of some of the previously proposed devices are disclosed in the following patents:

| U.S. PAT. NO. | PATENTEE |
|---|---|
| Re. 27,569 | Ackerman |
| 452,220 | Gunning |
| 552,832 | Fort |
| 623,022 | Johnson |
| 4,060,086 | Storz |
| 4,429,694 | McGreevy |

The McGreevy U.S. Pat. No. 4,429,694 discloses an electrosurgical generator for generating waveforms for electrosurgical fulguration.

The Ackerman U.S. Pat. No. Re. 27,569 discloses a catheter which is designed for insertion through the chest and into the heart specifically for the purpose of introduction of electrical stimulation during cardiac arrest. When the heart has ceased to beat, a generated impulse is provided which is capable of delivering electric current approximating in strength, frequency and distribution the normal current of the heart. No reference is made to a hollow catheter or to a tip thereof which can be supplied with sufficient power for removal of plaque or tissue from a blood vessel.

The Gunning U.S. Pat. No. 452,220 discloses a surgical electrode device in the form of a solid catheter composed of electrically discrete coaxially movable electrodes. The electrodes of Gunning are connected to a battery so that direct current may be introduced to an organ or part of the body after the device is inserted through a body orifice. The Gunning catheter is not hollow, does not use high frequency current and is used in a different manner and for a different purpose than the device of the present invention.

The Fort U.S. Pat. No. 552,832 discloses a catheter for treatment of strictures in body orifices, e.g. urethra, esophagus, uterus or rectum. The catheter includes one electrode in the middle of the catheter which is defined by a bowed platinum plate or wire which projects to one side of the catheter. Another electrode is applied externally to the body, for example, on the abdomen whereby current is passed through the stricture and acts "electrolytically or electrochemically thereupon". Fort does not teach a hollow electrode tip catheter which can be used for eroding tissue in vessels.

The Johnson U.S. Pat. No. 623,022 discloses a catheter which is adapted for insertion into a body cavity and which is allegedly capable of delivering an electric current to the body. The electric current was believed to have some curative powers and no reference is made in this patent to erosion of plaque or tissue in a vessel. The catheter can be used for delivering fluid into the body and the electric current allegedly flows from the catheter through the fluid into the body.

No metallic surface comes into contact with the mucous surface, and hence, the current is not concentrated at any point of contact, but is diffused by the liquid so that comparatively heavy current may be used without harm to the body parts. There is no teaching of high frequency current, bipolarity, or electro-surgery in the Johnson patent and this catheter is clearly used in an electrochemical manner and not for electrical erosion of plaque or tissue.

The Storz U.S. Pat. No. 4,060,086 discloses an endoscope which is an instrument for visually examining the inside of a hollow organ. This particular endoscope includes a loop-like electrode and has a body which is inflexible and which is not designed for use in cleaning blood vessels but which is arranged for transurethral operations. Cutting action is carried on by an inner cutting edge of the endoscope in combination with an electrically charged loop of wire which sparks. The exact mechanism and its operation are unclear. A washing agent is supplied and discharged through the endoscope.

As will be described in greater detail hereinafter, the device and method of the present invention for resolving atherosclerotic plaques and unwanted tissue differ from the devices and methods previously proposed by providing a catheter which is sized to be received in a blood vessel and which has an erosion electrode localized near a hollow tip member mounted at the distal end of the catheter. The catheter is flexible and therefore manipulatable into and through the lumen of a blood vessel and can be positioned therein proximate atherosclerotic plaque or unwanted tissue in the blood vessel. High frequency high voltage electric current is generated and supplied to the atherosclerotic plaques or tissue for a predetermined period of time to resolve the plaque or tissue. In particular, the erosion resulting from high frequency high voltage current about the electrode positioned proximate the tip of the device member actively resolves plaque or erodes tissue.

In one preferred embodiment of the device of the present invention, there is provided a tubular hollow tip member open at the distal end thereof and communicating with a flexible and elongated hollow catheter body. The eroded debris resulting from the intermittent application of high frequency high voltage current about the electrode is conveniently carried out of the catheter by a trident connection at the proximal end. In between applications of the current, a low voltage direct current is passed through the plaque or tissue for making an impedance measurement to determine if a sufficient amount of plaque has been resolved or tissue eroded.

The electrosurgical device of the present invention employs the application of electric current directly to an area of plaque or tissue buildup for resolving, ablating or removing the buildup and differs from copending U.S. application Ser. No. 536,852 filed Sep. 28, 1983 by Harold Herschenson for: PLAQUE RESOLVING DEVICE AND METHOD, which resolves plaque by heating plaque with a heat conductive member at the tip of a catheter heated by an electric coil.

SUMMARY OF THE INVENTION

According to the invention, there is provided a method for resolving atherosclerotic plaque buildup and/or eroding unwanted tissue in a blood vessel including the steps of: inserting an electrode in and along the lumen of a blood vessel; manually manipulating said electrode through the blood vessel; positioning said electrode proximate to atherosclerotic plaque buildup site or unwanted tissue site in the blood vessel; supplying a predetermined high frequency high voltage electrical current to said electrode; maintaining said predetermined current for a predetermined time period; and sensing from time to time the amount of plaque or unwanted tissue at the site.

Further, according to the invention, there is provided an electrosurgical plaque resolving or tissue eroding device adapted to be inserted within and along the lumen of a blood vessel and manipulated therethrough to a desired position where the device is operated to resolve atherosclerotic plaque buildup or erode tissue in the blood vessel to re-establish desired blood flow through the blood vessel or to remove tissue therefrom, said device comprising: an elongate flexible hollow tubular body having a distal end and a proximal end; a hollow tip member mounted at said distal end of said flexible hollow tubular body; an electrode associated with said hollow tip member for resolving plaque or eroding tissue; means for supplying a high frequency high voltage electrical current to said electrode; and means for sensing from time to time the amount of plaque or tissue at the site in the blood vessel.

Preferably, the hollow tip member, the distal end of the flexible hollow tubular body and the flexible hollow tubular body has a passage for withdrawing resolved eroded debris. Similarly, the proximate end of the body can include a "Y" or trident connection for facilitating removal of resolved matter and debris. Also, a passage for supplying a flushing fluid to the site may [also] be provided.

BRIEF DESCRIPTION OF THE DRAWINGS

FIG. 5 is an axial cross sectional view of a proximal end portion and a distal end portion of another embodiment of a plaque resolving or tissue eroding device constructed according to the teachings of the present invention.

FIG. 6 is an enlarged axial cross sectional view of the distal end portion of the device shown in FIG. 5.

FIG. 7 is a radial sectional view of the device shown in FIG. 6 and is taken along line 7—7 of FIG. 6.

FIG. 8 is another radial sectional view of the device shown in FIG. 6 and is taken along line 8—8 of FIG. 6.

FIG. 9 is a distal end view of the device shown in FIG. 6 and is taken along line 9—9 of FIG. 6.

DESCRIPTION OF THE PREFERRED EMBODIMENT

Figure 1:
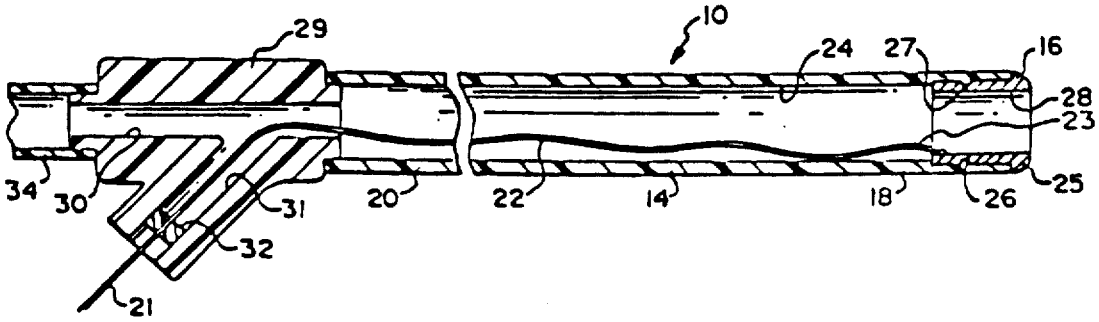
FIG. 1 is a fragmentary axial cross-sectional view of one embodiment of a plaque resolving or tissue eroding device constructed according to the teachings of the present invention and shows a monopolar electrode in the tip of the device adapted to be connected to a source of high frequency high voltage current.

Referring now to FIG. 1, there is illustrated therein a plaque and tissue resolving device constructed according to the teachings of the present invention and generally identified by reference numeral 10. The device 10 is adapted to be inserted within and along a lumen of a blood vessel and [manipulatable] *manipulated* therethrough to a position of atherosclerotic plaque or tissue buildup. The device 10 also can be referred to as a unipolar multilumen electrosurgical catheter 10.

The device 10 includes an elongate hollow tubular body or catheter 14 made of a flexible insulating material such as polyurethane and a hollow metal tip member 16, made of stainless steel, platinum, titanium or similar metal, mounted to a distal end 18 of the elongate tubular body 14. The metal tip member 16 is a monopolar electrode which supplies the electric current to a plaque buildup.

The return path for the current is through a large area, remote plate type, dispersive electrode typically placed onto a large, flat skin area on the patient, such as the thigh or belly.

The device 10 further is supplied by a high-frequency, high-voltage power supply coupled to proximal end 20 of the tubular body 14, and more particularly to a proximal end 21 of a wire conductor 22 that is connected to the hollow metal tip member 16 at its distal end 23. The wire conductor 22 extends through a hollow center passage 24 of the catheter body 14 between the tip member 16 and the high voltage power supply.

The tubular body 14 can be made of polyurethane, polyethylene or other biocompatible material which is suitable for intravascular use and which provides maximum flexibility to permit manipulation of the device 10 through a blood vessel to a desired position therein such as to a site of plaque buildup. The external and internal diameters of the tubular body 14 are sufficient to permit flexibility and adequate strength. Typically the tubular body 14 has a diameter approximately one third (⅓) the diameter of the blood vessel in which it is inserted.

The tip member 16 has a shaped distal end portion to facilitate insertion of the catheter 14 into and through a blood vessel. Moreover, there is a rounded, bevelled or chamferred nose 25 on tip member 16. The tip member 16 has a slightly smaller diameter than the body 14 whereby the distal end 18 extends over the outside of the tip member 16.

Also, an annular groove 26 is provided on tip member 16 for receiving a mating annular rib 27 on the inside of the distal end 18 of the tubular body 14 for holding the tip member 16 to the body 14. As shown, the tip member 16 has a central bore 28 which extends therethrough to communicate with the central passage 24 in the tubular body 14.

At the proximal end 20 there is a "Y" shaped fitting 29 made of polycarbonate or other suitable biocompatible material and having a straight through passage 30 and a branch passage 31. The wire conductor 22 passes through central passage 24 into the fitting 29 and through branch passage 31. A grommet 32 is located in passage 31 for positioning wire 22 and for preventing flow of fluid through branch passage 31.

At both ends of the fitting 29 there are counterbored recesses to receive therein the proximal end 20 of the catheter 14 near to proximal end 20. Similarly, a tube 34 fits inside and extends from the opposite end of fitting 29(away from the catheter 14) to deliver flushing fluid to or carry resolved debris away from the distal end 18.

A Bovie "Specialist" 75 watt E-S, Electro-Surgery Unit or similar Valleylabs unit can be used for the power supply.

The device 10 is used for ablating arteriosclerotic plaques, clots, etc. from viscera by supplying, to a site of plaque buildup, for example, a high-frequency, high-voltage current. Suction or irrigation can be applied to the straight passage 30 of the fitting 29 for removing debris during the ablating procedure.

Figure 2:
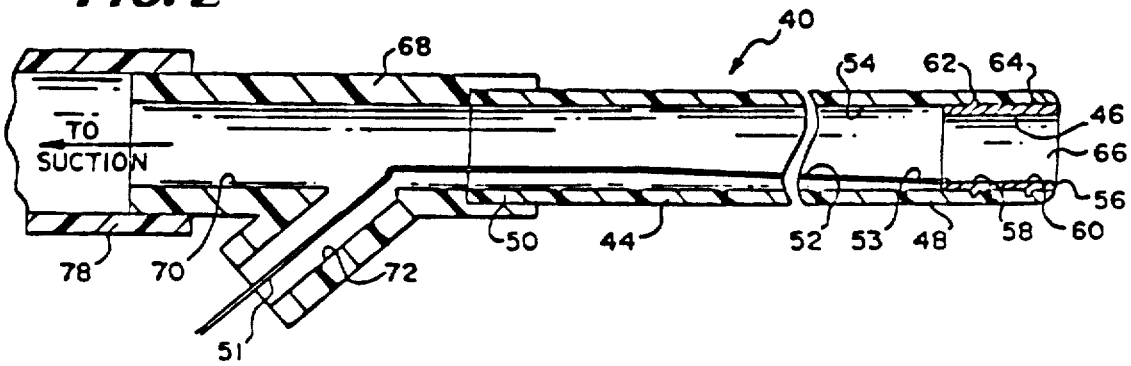
FIG. 2 is a fragmentary axial cross-sectional view of another embodiment of the device constructed according to the present invention and shows a monopolar electrode extending through the tip of the device.

In FIG. 2 is illustrated another embodiment of the plaque resolving or tissue eroding device of the present invention which is generally identified by the reference numeral 40. The device 40 also is adapted to e inserted along the lumen of a blood vessel and manipulatable therethrough to a position of atherosclerotic plaque or tissue buildup.

The device 40 includes an elongate hollow tubular body or catheter 44 made of an insulating material such as polytetrafluoroethylene sold under the trademark TFE TEFLON TM and a tip member 46 made of a modified stainless steel hypodermic tubing and mounted to distal end 48 of the elongate tubular body 44. The tip member could also be made from platinum, tantalum, aluminum or any other bio-compatible metal. Similarly some ultra thin insulating layers can be used, such as ceramic metal oxides or plastic over metal, for capacitively coupling electrical energy to tissue. The metal tip member 46 is a monopolar electrode which supplies the electric current to the plaque or tissue buildup.

The device 40 further includes a high-frequency, high-voltage electrical power supply (not shown) coupled to proximal end 50 of the tubular body 44 and more specifically to proximal end 51 of wire conductor 52.

Preferably, the wire conductor 52 is welded at its distal end 53 to the hollow metal tip member 46. The wire conductor 52 extends within a lumen 54 between the power supply and the tip member 46.

The tubular body 44 is made of a plastic, such as TEFLON TM, a material which is suitable for intravascular use, which provides maximum flexibility so as to permit manipulation of the device 40 through a blood vessel to a desired position therein and which can withstand the high temperatures and voltage gradients briefly generated during the flow of the high-frequency, high-voltage cutting currents.

The external and internal diameters of the tubular body 44 are sufficient to provide flexibility and adequate strength. Typically the tubular body 44 has a diameter approximately one third (⅓) the diameter of the blood vessel within which it is inserted.

As shown, the tip member 46 has an annular end edge 56 designed for coring. The tip member 46 is of smaller diameter than the catheter 44 whereby the distal end 48 of the catheter 44 extends over part of the outside of the tip member 46. Two circumferential grooves 58,60 are formed on the inside wall of catheter 44 for receiving mating annular ribs 62,64 on the outside of the tip member 46 for connecting the tip member 46 to the body 44.

The tip member 46 has a central bore 66 which extends therethrough to communicate with the central lumen 54 in tubular body/catheter 44.

At the proximal end 50 of the catheter 44, a "Y" shaped fitting 68 having a straight through passage 70 and a branch passage 72 is bonded onto the proximal end of the catheter 44. The wire conductor 52 passes through central lumen 54 into the fitting 68 and through branch passage 72. Suction applied to a tube 78 connected to the proximal end of fitting 68 will draw off debris resolved by the tip member 46.

The operation of device 40 is similar to that described in connection with device 10 of FIG. 1 in terms of the power supply used and the procedure for use. It should be appreciated, however, that the construction of FIG. 2 can function at high power levels because of the use of a TEFLON TM catheter 44.

The inside diameters of lumen 54 and fitting passage 70 are substantially the same in the device 40 so that accumulation of debris therein is minimized. Also, the suction tube 78, which can be made of TGGON TM plastic tubing, is of larger inside diameter and is received over the proximal end of fitting 68, either directly or by means of a quick-connecting fitting.

The passage 72 can be closed with a seal grommet, if desired, or can be used for delivering flushing fluid to the tip member 46 in between applications of suction to fitting 68.

Figure 3:
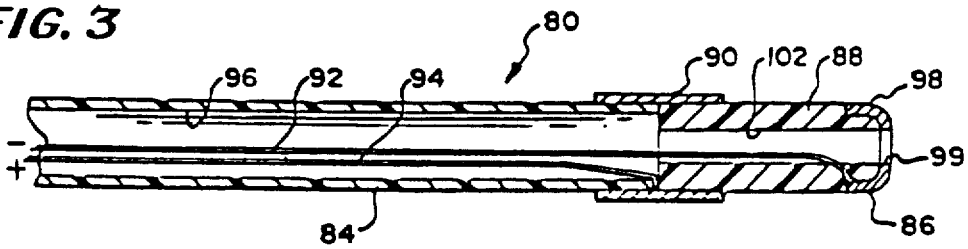
FIG. 3 is a fragmentary axial cross-sectional view of the distal end portion of another embodiment of the device constructed according to the present invention and shows a bipolar electrode assembly at a distal end of the body.

Referring now to FIG. 3, there is illustrated another plaque and tissue resolving device constructed according to the teachings of the present invention and generally identified by reference numeral 80. The device 80 is adapted to be inserted in and along the lumen of a blood vessel and is manipulatable therethrough to a position of atherosclerotic plaque or tissue buildup. The device 80 includes an elongated hollow tubular body or catheter 84 made of an insulating material such as RTV silicone rubber or thermoplastic material which is resistant to the effects of high temperature and is very flexible. A first electrode forming hollow metal tip member 86 is mounted to the distal end of an insulative sleeve or spool 88 made from a relatively high temperature dielectric material, such as alumina, ceramic or polyimide polymer. This insulating sleeve 88 is bonded inside a secondary sleeve electrode 90. The conductive hollow tip member 86 is separated from the secondary sleeve electrode 90 by the insulating spool 88. In use, electric current is applied to the plaque or tissue buildup across or between the electrodes 86 and 90.

The device 80 further includes a high-frequency, high-voltage electric current power supply (not shown) similar to power supplies referred to above.

Wire conductors 92 and 94 are connected respectively to electrodes 86 and 90 through openings in the insulating spool 88 and the catheter 84 and extend therefrom through a hollow center lumen 96 of the catheter 84 to the high-frequency, high-voltage power supply. Alternatively, the conductors 92 and 94 can be contained within subsidiary lumens in the catheter body 84. These subsidiary lumens are not shown for clarity, but their incorporation may be preferable when it is desired to increase the separation of the two conductors 92,94. In order to provide the subsidiary lumens for the two conductors 92 and 94, it is, of course, necessary to reduce the diameter of the primary lumen 96. Thus, a compromise is established between electrical characteristics and flushing efficacy which must be optimized for each specific application of the device 80. Even though the device 80 includes bipolar electrodes 86 and 90, the operation of the device 80 is substantially the same as the operation of the devices 10 and 40.

The tubular body 84 is preferably made of a silicone rubber, a material which is suitable for intravascular use and which provides extreme flexibility so as to permit manipulation of the device 80 through a blood vessel along for instance a guide wire (not shown) to a desired position.

Alternative materials, such as high-temperature thermoplastic fluorocarbon polymers (e.g. ethylene-chlorinated tetrafluoroethylene or fluorinated ethylene-propylene) may also be used for the catheter body 84. The external and internal diameters of the catheter tubular body 84 are sufficient to allow extreme flexibility and yet have adequate strength. The guide wire would be non-conductive and of small diameter to prevent interference with the electrodes.

The tip member 86 may be positioned against an area of atherosclerotic plaque or tissue buildup during the insertion process of the device 60. The tip member 86 has a curved or bevelled forward edge 98. The electrodes 86 and 90 are insulated from each other by insulative spool 88. As shown, the tip member 86 is generally cup-shaped and has a central distal opening 99 which extends beyond the insulating spool 88 and communicates with a central passage 102 within spool 88. The passage 102 communicates through spool 88 to the lumen 96 of catheter 84.

A "Y" or trident shaped fitting can be connected to a proximal end (not shown) of catheter 84. The wire conductors 92 and 94 extend from electrodes 86 and 90 through central lumen 96 for connection to a high-frequency, high-voltage power supply (not shown).

In operation, the bipolar electrodes 86 and 90 of the device 80 will conduct current to and from an area of plaque or tissue buildup which is eroded by the current. Any debris from this procedure then can be removed along lumen 96 by means of suction applied to the proximal end of the catheter 84. In use, the catheter might be introduced into the vessel and directed past the area of atherosclerotic plaque; the catheter would then be withdrawn through the plaque while suction is applied to the lumen 96 of the catheter and while high-voltage, high-frequency current is applied to the electrodes 86 and 90 to reduce and resolve the narrowing of the artery caused by the presence of the plaque. Alternatively, the catheter may be advanced through the plaque while suction and high-voltage, high-frequency current are applied, as described above for device 10.

Figure 4:
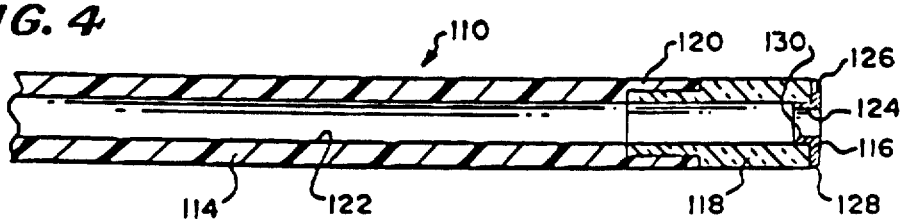
FIG. 4 is a fragmentary axial cross-sectional view of another embodiment of a device constructed according to the present invention and shows a monopolar electrode at a tip of the device.

In FIG. 4 there is illustrated another embodiment of the device of the present invention which is generally identified by reference numeral 110 and which includes an elongate hollow tubular body or catheter 114 made of a flexible insulating material, such as described above, and a hollow metal tip member 116 mounted to a support 118 which in turn, is mounted to a distal end 120 of the elongate tubular body 114. The metal tip member 116 is a monopolar electrode which supplies electric current to an area of plaque or tissue buildup. The device 110 is powered by a high-frequency, high-voltage power supply coupled to a proximal end (not shown) of the tubular body 114.

At least one insulated wire conductor (not shown) is connected to and extends from the hollow metal tip member 116 through a hollow center lumen 122 of the catheter 114 to the high-frequency, high-voltage power supply (not shown).

Alternatively, the wire conductor may extend from the proximal end of the catheter to the distal electrode tip member 116 by means of a secondary small lumen in the body or catheter 114, thus preventing fouling of the central lumen 122 by the conductor and protecting the conductor. The support 118 is an insulator and preferably is constructed of glass or ceramic to withstand any heat generated at the electrode tip member 116.

The catheter/tubular body 114 is made of polymeric material which is suitable for intravascular use and which provides maximum flexibility so as to permit manipulation of the device 110 through a blood vessel to a desired position in the blood vessel. The external and internal diameters of the tubular body 114 are sufficient to permit flexibility and strength and also permit adequate flow.

The tip member 116 is hollow mushroom-shaped, or [a] hollow stove pipe hat shaped with a bore 124 therethrough. A cap portion 126 is rounded or bevelled at its outer radius as indicated at 128, and a stem portion [130] *129* extends into the interior of the tubular insulator/support 118. The bore 124 communicates with the central lumen 122 in the tubular body 114.

A "A" or trident-shaped fitting can be connected to the proximal end (not shown) of the catheter body 114.

In use, the device 110 functions as a monopolar electrode similar to the electrodes 16 and 46 in the devices 10 and 40. The glass or ceramic support 118 is advantageous because of its high insulative properties and heat resistance.

Also, it provides a structure on the end of the flexible thin-walled hollow polymeric tubular body 114 for mounting and carrying the tip member 116.

One preferred embodiment of a device constructed according to the teachings of the present invention is illustrated in FIGS. 5-9 and is generally identified therein by reference numeral 130. The device 130 includes a catheter or elongate tubular body 131 having a distal end 132, a proximal end 133, a central lumen 134 and first and second radially outwardly located lumens 135 and 136. The catheter 131 is preferably made of polyurethane. The distal end 132 has an isolation collar 137 made of a high-melting point plastic such as, but not limited to, silicone, TFE (tetrafluoroethylene), polyphenylenesulfide, or ceramic or glass, mounted thereto. Mounted to and within the collar 137 is a hollow metal tip member or electrode 138 made of stainless steel, platinum, titanium or similar electrode material.

As shown, the metal tip member 138 is fully received within a countersunk cavity 139 in the collar 137 and has a bore 140 which mates with, and is flush with, a bore 141 in the collar 137. An annular front surface 142 of tip member 138 is flush with a front surface 143 of the collar 137 which surface 143 has a bevel or round 144 at its largest radius. The bore 141 mates with and is flush with the central lumen 134.

The lumen 135 opens onto outer cylindrical surface 145 of body 131 at a port 146 in the distal end 132 just behind collar 137. Flushing fluid, such as deionized water, is supplied to the lumen 135 through a connector fitting 147 made of polycarbonate and a tube 148 made of polyurethane coupled at an angle to the proximal end 133 of the tubular body 131 as shown. The coupling of tube 148 to the catheter body 131 may also be accomplished by means of a bonded or molded-on plastic connector, not shown.

Another fitting 149 and tubing 150 are coupled at an angle to the proximal end 133 of the tubular body 131 and communicate with lumen 136 which together form a passageway for a wire or ribbon conductor 151 made of copper, silver, nickel or other suitable electrically conductive material.

The conductor 151 extends to and into the collar 137 and is soldered or welded at 152 to the tip member 138. The tubing 150 may alternatively be connected to the body 131 by a separate part as described for tube 148.

A connector 154 made of polycarbonate is coupled axially to the proximal end 133 of the tubular body 131 which is received in a cavity 155 in the connector 154. The connector 154 has a central lumen 156 mating with and flush with the lumen 134. The proximal end of connector 154 may contain a tapered connection opening such as a standard Luer taper socket.

In use, a negative pressure or suction is applied to the connector 154 for withdrawing debris from a blood vessel while an electric current is applied to plaque or tissue by the device 130, which can be referred to as an electrosurgical catheter.

Also in use, a heavily insulated guidewire or stylet 157 is passed through the lumen 134 which has a diameter approximately one-half (½) the diameter of tubular body 131 for stiffening the device 130 and for guiding the tip member 138 to a desired site in a blood vessel. The guidewire 157 may have a metal core 158 surrounded by a thick layer of insulating material 159 such as silicone or polytetrafluoroethylene.

The device 130 is a unipolar device, and the return current path for this device is provided by a plate-like, dispersing electrode (not shown) which is usually placed onto a large, flat skin area on the patient, such as the thigh or belly.

Figure 10:
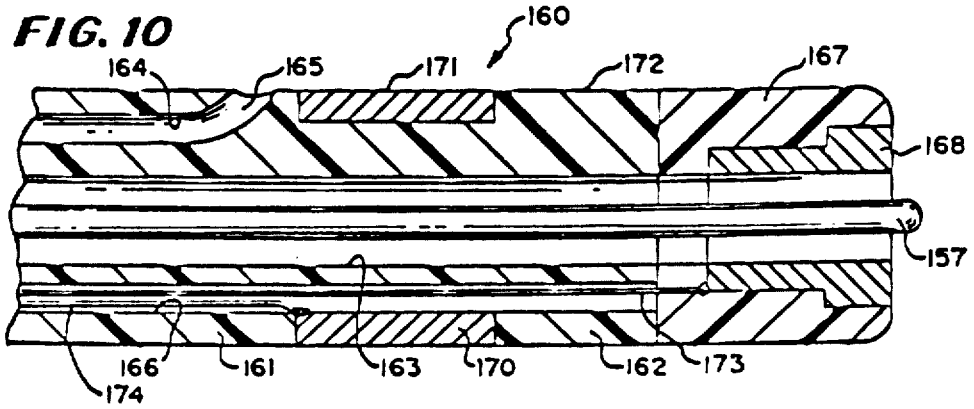
FIG. 10 is an axial cross sectional view of a distal end portion of another embodiment of the plaque resolving or tissue eroding device constructed according to the teachings of the present invention.

In FIG. 10 is illustrated an axial cross-sectional view of another device 160 constructed according to the teachings of the present invention. More particularly, a distal end portion of the device 160 is shown in FIG. 10. Here, a tubular body 161 having a distal end 162, a central lumen 163, a flushing lumen 164 with an outlet port 165 and a conductor-carrying lumen 166 has a collar 167 mounted to the distal end 162 with a tip electrode 168 mounted in the collar 167 and a second ring electrode 170 mounted around the distal end 162 of the body 161 and spaced between the port 165 and the collar 167. Preferably, as shown, the ring or band electrode 170 is recessed in the body 161 so that outer surface 171 thereof is flush with outer surface 172 of the body 161.

For this bipolar device 160, two insulated wire conductors 173 and 174 are received in the lumen 166 and welded or soldered respectively, to electrodes 168 and 170 at 175 and 176. It may be more desirable, however, to provide separate conductor-carrying lumens to better insulate the conductors 173 and 174 from each other to minimize the possibility of a short circuit between them.

It will be understood that, in use of the device 160, current will flow between the electrodes 168 and 170 through plaque or tissue buildup that it is desired to remove. Owing to the smaller tissue-contact area of the tip electrode 168 compared to that of the band electrode 170, the electrosurgical action will be concentrated at the tip electrode, resulting in a coring or ablative removal of tissue or plaque.

Figure 11:
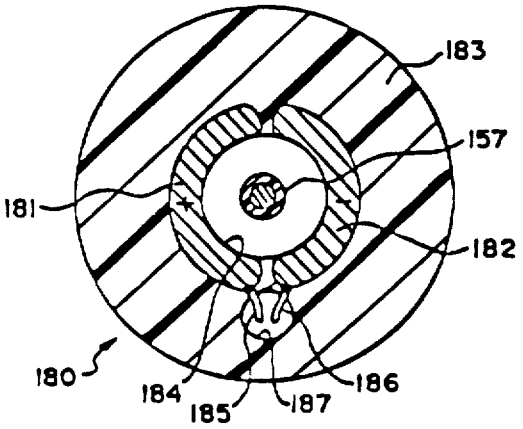
FIG. 11 is a radial sectional view, similar to the sectional view shown in FIG. 8, through a distal end portion of another embodiment of the plaque resolving or tissue eroding device of the present invention and shows a modified electrode construction.
Figure 12:
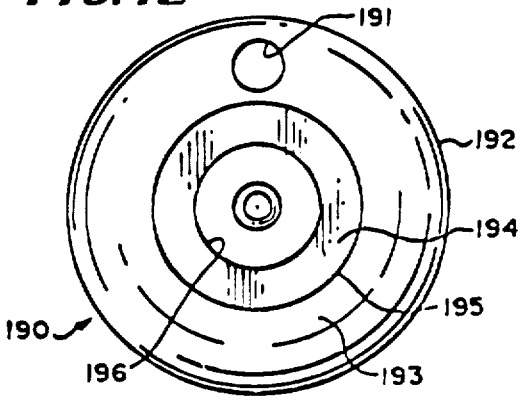
FIG. 12 is an end view, similar to the end view shown in FIG. 9, of a distal end of another embodiment of a device constructed according to the teachings of the present invention and shows a flushing port opening axially onto the distal end.
Figure 13:
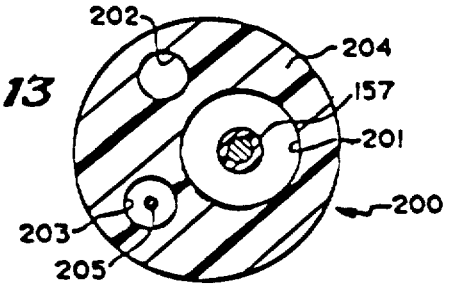
FIG. 13 is a radial sectional view, similar to the view shown in FIG. 7, through a distal end portion of still another embodiment of a plaque resolving or tissue eroding device constructed according to the teachings of the present invention and shows an eccentric positioning of a central lumen in a tubular body of the device and two other lumens resulting in a tubular body of minimum diameter.

Other electrosurgical catheter embodiments are shown in FIGS. 11, 12 and 13. In FIG. 11, a radial cross-section of one electrosurgical catheter device 180 is shown. Here, two semi-cylindrical tip electrodes 181 and 182 are mounted within an insulative collar 183 and face each other across a central lumen 184 in the collar 183. Insulated wire conductors 185 and 186, welded or soldered to the respective electrodes 181 and 182, extend rearwardly into a wire-carrying lumen 187. Again, if desired, separate wire-carrying lumens can be provided. The cross-section shown in FIG. 11 is similar to, and is, taken along a similar section line as [is], the cross-section shown in FIG. 8. Through the use of this configuration, bipolar electrosurgical currents can be created directly at the catheter distal tip without the need for a secondary band electrode, and eliminating the need for a patient dispersive plate.

FIG. 12 is an end view, similar to the end view shown in FIG. 9, of another electrosurgical catheter device 190 which has a flushing lumen 191 extending in a tubular body and end collar 192 straight through to, and opening onto, a front surface 193 of the collar 192 radially outwardly from a front surface 194 of tip electrode 195 and a central lumen 196. The flushing lumen 191 then opens closer to the opening of the central suction lumen 196 at the very tip of the device 190. Alternatively, the single flushing lumen 191 may branch to several outlet openings at several circumferential positions at the tip of the catheter, resulting in a more uniform supply of flushing liquid.

FIG. 13 is a sectional view, similar to the view shown in FIG. 7, of still another electrosurgical device 200 which has eccentrically located lumens 201, 202 and 203 in a tubular body 204, lumen 201 being a suction lumen 201, lumen 202 being a flushing lumen 202, and lumen 203 being a wire carrying lumen 203 which carries a wire conductor 205.

The eccentric locating of the lumens 201-203 provides a more compact tubular body 204 with a smaller diameter than if the lumens 201-203 were located in the manner shown in FIG. 7.

Figure 14:
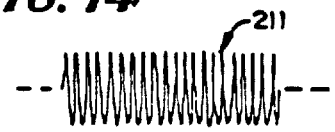
FIG. 14 is a graph of a pure sine wave power waveform that is applied to plaque or tissue at a site in the body during a cutting mode of operation of one of the devices illustrated in the previous figures.
Figure 15:
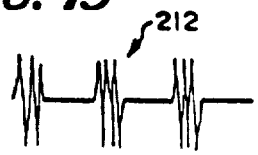
FIG. 15 is a graph of a high-frequency, power-pulse waveform that is applied to plaque or tissue at a site in the body during a coagulation mode of operation of one df the devices illustrated in the previous figures.
Figure 16:
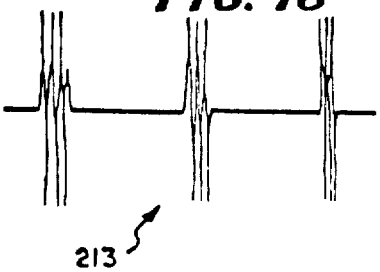
FIG. 16 is a graph of a high-frequency, low-duty-cycle, power-pulse waveform that is applied to plaque or tissue during a coagulation mode of operation of one of the devices illustrated in the previous figures.

FIGS. 14,15 and 16 illustrate three waveforms 21, 212 and 213 of the high-frequency, high-voltage electrical current that is applied by the device 10,40,80,110,130,160, 180,190 or 200. A pure cut sine waveform is shown in FIG. 14 and two coagulation mode waveforms having high power pulses are shown in FIGS. 15 and 16. The Bovie "specialist" ElectroSurgery power supply unit can be used and has 75 watt capability but higher voltage power supplies may be necessary in certain circumstances. An oscillator circuit is used to generate the high-frequency waveforms.

As shown in FIG. 14, the sine waveform 21 is used for cutting and is symmetrical about its center and relative to its peaks. This form of electrical power is effective to resolve material buildup by achieving a clean cutting action.

The coagulation mode waveforms 212 and 213 have spurts of high sinusoidal power pulses separated by no pulses and are generated by an oscillator including a solid state switching device. The coagulation mode waveforms 212 and 213, having definite pulses of high power, allow higher peak electrical power to be applied while limiting the average electrical power; by so doing, it is possible to apply the high power levels necessary to ablate insulative plaque deposits without causing excessive heating to nearby tissues or to the catheter itself. The waveform 213 differs from waveform 212 by having high amplitude current peaks with a smaller duty cycle, i.e., a longer time period between each spurt of pulses. The high-frequency, high-voltage, low-duty-cycle waveform 213 includes shorter spurts of pulses of high power at high-frequency separated by longer periods of no power. As explained, this type of power output is particularly useful in creating localized, superficial ablation while reducing the damage to underlying tissue. Electrical waveforms of this very low-duty-cycle type cannot be produced by standard electrosurgical generators. A specialized generator of similar design is needed for the production of this type of electrical current.

In use, one of the electrosurgical catheter devices 10,40,80,110,130,160,180,190 or 200 is inserted into the appropriate blood vessel. Under fluoroscopic control, the catheter 10 or 40,80,110,130,160,180,190,200 is advanced over the guidewire 157 to the lesion or area of atherosclerotic plaque buildup which has caused stenosis of the blood vessel.

As the catheter is advanced, deionized water or a non-conducting solution is flushed through one of the flushing lumens. This lumen is also used for injecting a radio-opaque dye into the blood vessel at the site of stenotic buildup to confirm proper catheter placement.

In addition, or alternatively, impedance measurements across the electrodes of the device can be made using a low-voltage DC current to determine, by the magnitude of the impedance, the amount of plaque buildup between the electrodes.

The catheter is then advanced while a high-frequency, high-voltage current, either pure sine wave (211) or periodic pulses (212 or 213), is supplied intermittently to the electrodes. Typically, the frequency will be between 0.5 and 20 megahertz and the voltage will have a magnitude or several hundred volts.

Preferably, alternating "coring" and "measuring" is performed. In this respect, the "coring" high voltage, high-frequency current is applied for a short time period followed by application of low-voltage DC current for measuring impedance related to the amount of buildup remaining.

It will be appreciated that by simultaneous controlled movement of the catheter and controlled intermittent application of high-voltage, high-frequency and alternate impedance measuring, the catheter, in effect, "cores" through the stenotic area to create a lumen of known diameter. At the same time, flushing fluid as well as suction is supplied to the site of coring to wash away and then evacuate any debris.

Confirmation of complete plaque or tissue removal is determined by injection of radio-opaque dye into the vessel at the site during X-ray visualization of the "cored" vessel; or it is determined by impedance measurements.

A variety of devices, 10,40,80,110,130,160,180,190 and 200 have been described and explained herein for use in resolving plaque or eroding tissue in blood vessels. These devices 10,40,80,110,130,160,180,190 and 200 have application in connection with not only resolving plaque, but also in connection with clearing hepatic and bile ducts and liver tissue in general where hepatic flow must be corrected. Similarly, such devices 10,40,80,110,130,160,180,190 and 200 can be used to revascularize and smooth muscle coring in cardiac revascularization, and in other procedures such as, for example, the ablation of: a) ectopic foci, in treatment of tachycardia, or b) removal of tissue in the central nervous system of carcinomas, without damage to surrounding tissue. Skilled artisans will know that any of the devices 10,40,80,110,130,160,180,190 and 200 described above can be modified by combining portions thereof with other structural arrangements as disclosed herein.

Accordingly, the devices 10,40,80,110,130,160,180, 190 and 200 can be modified without departing from the teachings of the present invention and it is to be understood that the scope of the invention is only to be limited as necessitated by the accompanying claims.

We claim:

1. An electrosurgical plaque-resolving or tissue-eroding device having a distal end which is insertable within and along the lumen of a blood vessel and [manipulated] *manipulatable* therethrough to a desired position without causing undue trauma where the device is operated to thermally resolve atherosclerotic plaque buildup or erode tissue in the blood vessel to re-establish desired blood flow through the blood vessel or to remove tissue therefrom, said device comprising: an elongate flexible hollow tubular body having a distal end, a proximal end, and a diameter smaller than the diameter of the vessel into which said device is inserted; first passage means within said tubular body for supplying a flushing fluid to the site where plaque or tissue is resolved or eroded; second passage means within said tubular body for evacuating, such as by suction, debris at the site of resolving plaque or eroding tissue from the site; a hollow tip member mounted at said distal end of said flexible hollow tubular body; an electrode adjacent to and in operative association with said hollow tip member for resolving plaque or eroding tissue, said tip member being beveled or rounded at the distal end of said device; means for supplying a high-frequency electrical current to said electrode for cutting tissue or coagulating body fluid; and means for sensing, from time to time, the amount of plaque or tissue at the site in the blood vessel.

2. The device of claim 1 wherein said hollow tip member is an electrode.

3. The device of claim 2 wherein said hollow tip member is made of stainless steel.

4. The device of claim 2 wherein said electrode has the shape of a stove pipe hat having its top removed, with the brim shaped portion of said electrode being at the distal end of said device.

5. The device of claim 2 wherein said electrode is an unobstructed ring electrode positioned within said first passage means of the hollow tip member, a distal end of said ring electrode being flush with the end of said tip member.

6. The device of claim 2 wherein said electrode has the shape of a hollow mushroom including a head which is situated at the distal end of the device.

7. The device of claim 2 including an electrical insulator which has a high temperature melting point and which connects said tip member electrode to said tubular body.

8. The device of claim 7 including a ring electrode between said electrical insulator and said tubular body to form said device as a bipolar device.

9. The device of claim 7 wherein said insulator is made of a material selected from the group consisting of glass, ceramic, fluorocarbon polymers, polyimide polymers and polyphenylene sulfide.

10. The device of claim 7 wherein said insulator has an inwardly stepped formation and said electrode is cup shaped, with a portion of its bottom removed, and is attached to a distal end of said electrical insulator with the cup walls surrounding said stepped formation.

11. The device of claim 1 wherein said electrode is covered with an ultra thin layer of insulation on the surface thereof which contacts the plaque or tissue buildup.

12. The device of claim 1 wherein said hollow tubular body is made of silicone rubber.

13. The device of claim 1 wherein said hollow tubular body is made of polyurethane.

14. The device of claim 1 wherein said hollow tubular body is made of polytetrafluoroethylene.

15. The device of claim 1 wherein said hollow tubular body is made of a polymeric substance capable of resisting softening during resolving.

16. The device of claim 1 wherein said hollow tip member is made of aluminum.

17. The device of claim 1 wherein said hollow tip member is made of tantalum.

18. The device of claim 1 wherein said hollow tip member is made of platinum.

19. The device of claim 1 wherein said high-voltage, high-frequency current supply means is capable of generating a pulsed current waveform having an intermittent group of pulses separated by periods of no current and being adapted for use in a coagulation mode of operation of said device.

20. The device of claim 19 wherein said pulsed current waveform has high voltage peaks and a low duty cycle.

21. The device of claim 1 wherein said high-voltage, high-frequency, current supply means is capable of generating a current waveform having a pure sine waveform.

22. The device of claim 1 wherein said high-voltage is several hundred volts.

23. The device of claim 1 wherein said high frequency is between 0.5 1 and [20] *8* megahertz.

24. The device of claim 1 wherein said sensing means further includes radio-opaque dye and X-ray viewing means, said radio-opaque dye being injected into the blood vessel at the site and the X-ray image showing the amount of plaque remaining being displayed on said viewing means.

25. The device of claim 1 further including a third passage means for carrying at least one conductor.

26. The device of claim 25 wherein said passage means are arranged with their axes contained within the diameter of said tubular body.

27. The device of claim [21] *25* wherein said passage means are arranged with their axes eccentric of the axis of said tubular body.

28. The device of claim 25 wherein said first passage means opens onto a cylindrical side wall surface of said tubular body at a location adjacent said tip member.

29. The device of claim 25 wherein said first passage means extends through said tip [memeber] *member* and opens onto a front end surface of said tip member.

30. The device of claim 25 including a second electrode at the distal end of said tubular body.

31. The device of claim 30 wherein said tip member is made of a relatively high temperature resistance insulative material, said first electrode is mounted in said tip member and has an electrode surface on the distal end thereof, and said second electrode is a ring or sleeve electrode on said tubular body and located adjacent but rearwardly of said tip member.

32. The device of claim 30 wherein said tip member is made of a relatively high temperature resistance insulative material, and said first and second electrodes are semi-cylindrical in shape and are positioned [with said tip member] facing each other across the axis of said tip member.

33. The device of claim 30 including a fourth passage means for carrying a second wire conductor therein for connection to said second electrode.

34. The device of claim 25 including a trident structure at the proximal end of said tubular body, said trident structure having three legs each of which has a passageway communicating individually with a respective one of said passage means in said tubular body.

35. The device of claim 25 including a stiffening wire which extends through said first passageway for stiffening said tubular body.

36. The device of claim 1 including a collar at said distal end of said device, said collar having a bore therein and a countersunk formation in said bore, a front flat surface and an outer generally cylindrical surface, said electrode being fully received within said countersunk formation, having a bore therethrough which mates with and is flush with said bore of said collar, and having an annular front surface which is flush with said front surface of said collar, and said collar being beveled or rounded between the front surface and the outer surface.

37. The device of claim 1 wherein said sensing means includes means coupled to said electrode for measuring the impedance between said electrode through the plaque or tissue buildup and a current return path, the impedance measured being directly related to the amount of plaque or tissue buildup at the site.

38. The device of claim 37 wherein said impedance measuring means include means for supplying a low voltage DC current to said electrode for making the impedance measurement.

39. A cardiovascular thermal ablation device having a distal portion which is insertable into and along a lumen of a blood vessel to a desired position against an area of atherosclerotic plaque buildup or like obstruction within the lumen of the vessel without undue trauma, said device having means for thermally resolving the area of obstruction within the vessel and having means for removing resolved tissue from the area of thermal ablation, said device further comprising an elongate flexible hollow tubular body having a distal end and a proximal end; a hollow tip member mounted at said distal end of said flexible hollow tubular body; at least one electrode adjacent to and in operative association with said hollow tip member for resolving plaque or eroding tissue, said tip member being beveled or rounded at said distal end of said device; means for supplying electrical current to said electrode; means for sensing, between periods of application of electrical current to said electrode, the amount of plaque or tissue remaining to obstruct the site in the blood vessel by measuring the impedance of the plaque [of] *or* tissue; means for supplying fluid to, or for supplying suction from, the site including at least one channel extending through said flexible hollow tubular body and tip member, and said device having at least one further channel, at least one wire conductor in said further channel extending proximally from said at least one electrode to said proximal end of said device and means for connecting said conductor to a source of *high frequency* electrical current.

*40. An electrosurgical plaque-eroding device having a distal end which is insertable within and along the lumen of a blood vessel and manipulatable therethrough without causing undue trauma to a desired position where the device is operated to thermally erode atherosclerotic plaque buildup in the blood vessel to reestablish desired blood flow through the blood vessel, said device comprising: an elongate flexible hollow tubular body having an inner lumen, a distal end, a proximal end, and an outer diameter smaller than the diameter of the vessel into which said device is inserted; a hollow tip member mounted at said distal end of said flexible hollow tubular body, having a distal end and a proximal end, and having an axial passageway therethrough communicating said tip member distal end with said lumen of said hollow tubular body; means for withdrawing material which collects at said tip member distal end; means for supplying flushing fluid to said tip member distal end; an electrode assembly adjacent to and in operative association with said hollow tip member and including first and second electrodes for thermally eroding plaque, said tip member being beveled or rounded at the distal end of said device to facilitate insertion thereof into a blood vessel, and means for supplying a high-frequency electrical current to said electrodes for cutting plaque, which high frequency can extend up to 20 megahertz.*

*41. The electrosurgical plaque-eroding device of claim 40 wherein said means for withdrawing material which collects at said tip member distal end and said means for supplying flushing fluid to said tip member distal end are both defined by the inner lumen of the tubular body and the axial passageway through the hollow tip member which provide passage means for withdrawing material which collects at said tip member distal end and for supplying flushing fluid to said tip member distal end.*

*42. A cardiovascular thermal ablation device having a distal portion which is insertable into and along a lumen of a blood vessel without causing undue trauma to a desired position against an area of atherosclerotic plaque buildup or like obstruction within the lumen of the vessel, said device having means for thermally resolving the area of obstruction within the vessel, said device further comprising an elongate flexible hollow tubular body having an inner lumen, a distal end and a proximal end; a hollow tip member mounted to said distal end of said flexible hollow tubular body having a distal end and a proximal end, and having an axial passageway therethrough communicating said tip member distal end with said lumen of said hollow tubular body; means for withdrawing material which collects at said tip member distal end; means for supplying flushing fluid to said tip member distal end; said means for thermally eroding plaque including an electrode assembly adjacent to and in operative association with said hollow tip member and including two electrodes for eroding plaque; said tip member being beveled or rounded at said distal end of said device; means for supplying high frequency electrical current to said electrodes, which high frequency can extend up to 20 megahertz; and means for sensing, between periods of application of electrical current to said electrodes, the amount of plaque remaining at said position by measuring the impedance through the plaque between said two electrodes.*

*43. The electrosurgical plaque-eroding device of claim 42 wherein said means for withdrawing material which collects at said tip member distal end and said means for supplying flushing fluid to said tip member distal end are both defined by the inner lumen of the tubular body and the axial passageway through the hollow tip member which provide passage means for withdrawing material which collects at said tip member distal end and for supplying flushing fluid to said tip member distal end.*

*44. An elongate electrosurgical plaque-eroding device having a distal end which is insertable within, through and long the lumen of a blood vessel without causing undue trauma to the blood vessel to a desired position where the device is operated to thermally erode atherosclerotic plaque buildup in the blood vessel to re-establish desired blood flow through the blood vessel, said device comprising: an elongate flexible body having an inner lumen, a distal end, a proximal end, and an outer diameter smaller than the diameter of the vessel into which said device is inserted; a tip section at said distal end of said elongate flexible body having a distal end and a proximal end, and having an axial passageway therethrough communicating said tip section distal end with said lumen of said hollow tubular body; means for withdrawing material which collects at said tip section distal end; means for supplying flushing fluid to said tip section distal end; an electrode assembly adjacent to and in operative association with said tip section and including first and second electrodes for thermally eroding plaque, said tip section being rounded at the distal*

*end of said device to facilitate insertion thereof into a blood vessel, and means coupled to said electrodes for supplying a high-frequency electrical current to said electrodes for cutting through said plaque, which high frequency can extend up to 20 megahertz.*

*45. The electrosurgical plaque-eroding device of claim 44 wherein said means for withdrawing material which collects at said tip section distal end and said means for supplying flushing fluid to said tip section distal end are both defined by the inner lumen of the tubular body and the axial passageway through the hollow tip section which provide passage means for withdrawing material which collects at said tip section distal end and for supplying flushing fluid to said tip section distal end.*

*46. A cardiovascular thermal ablation device having a distal portion which is insertable into and along a lumen of a blood vessel without causing undue trauma to a desired position against an area of atherosclerotic plaque buildup or like obstruction within the lumen of the vessel, said device having means for thermally resolving the area of obstruction within the vessel, said device further comprising an elongate flexible body having an inner lumen, a distal end and a proximal end; a tip section at said distal end of said elongate flexible body having a distal end and a proximal end, and having an axial passageway therethrough communicating said tip section distal end with said lumen of said hollow tubular body; means for withdrawing material which collects at said tip section distal end; means for supplying flushing fluid to said tip section distal end; said means for thermally eroding plaque including an electrode assembly adjacent to and in operative association with said distal end of said device; means coupled to said electrodes for supplying high frequency electrical current to said electrodes, which high frequency can be up to 20 megahertz; and means for sensing, between periods of application of electrical current to said electrodes, the amount of plaque remaining at said position by measuring the impedance through the plaque between said two electrodes.*

*47. The electrosurgical plaque-eroding device of claim 46 wherein said means for withdrawing material which collects at said tip section distal end and said means for supplying flushing fluid to said tip section distal end are both defined by the inner lumen of the tubular body and the axial passageway through the hollow tip section which provide passage means for withdrawing material which collects at said tip section distal end and for supplying flushing fluid to said tip section distal end.*

* * * * *